United States Patent [19]

Davis et al.

[11] 4,414,508

[45] Nov. 8, 1983

[54] METHOD AND APPARATUS FOR AUTOMATED INSPECTION OF FASTENER HOLES BY EDDY CURRENT

[75] Inventors: Hubert B. Davis, Tucker; Bonner W. Staff, Acworth; James A. Willis, Smyrna, all of Ga.

[73] Assignee: Lockheed Corporation, Burbank, Calif.

[21] Appl. No.: 249,016

[22] Filed: Mar. 30, 1981

[51] Int. Cl.³ .................. G01N 27/82; G01R 33/12; G05B 19/02
[52] U.S. Cl. .................. 324/238; 324/219; 324/225; 364/472; 364/483
[58] Field of Search .................. 324/219–221, 324/225, 235, 237, 210, 238, 216, 217; 364/580; 371/20, 24, 25

[56] References Cited

U.S. PATENT DOCUMENTS

| | | | |
|---|---|---|---|
| 2,939,073 | 5/1960 | Eul, Jr. | 324/238 |
| 3,718,855 | 2/1973 | Rogel et al. | 324/219 |
| 4,087,749 | 5/1978 | McCormack | 324/235 |
| 4,134,067 | 1/1979 | Woodbury | 324/219 |
| 4,193,028 | 3/1980 | Downs | 324/237 |
| 4,207,520 | 6/1980 | Flora et al. | 324/238 |
| 4,270,178 | 5/1981 | Lillig | 364/580 |
| 4,280,220 | 7/1981 | Vaeches | 364/580 |
| 4,351,031 | 9/1982 | Flaherty et al. | 324/238 |

*Primary Examiner*—Gerard R. Strecker
*Assistant Examiner*—Warren S. Edmonds
*Attorney, Agent, or Firm*—Albert L. Carter

[57] ABSTRACT

An automated eddy current fastener hole inspection apparatus and method for providing an automatic indication of the presence of a crack in structural members. The device automatically advances the probe of an eddy current instrument in a hole in the structural member, induces an eddy current, detects the eddy current signal produced by the eddy current instrument, digitizes the eddy current signal, analyzes the digitized signal for the presence of a characteristic signature corresponding to the effect of a crack in the structural member upon the eddy current signal, and alerts the operator of the presence of a crack or of noise conditions in the eddy current signal which may mask the presence of a crack. The device is responsive to contiguous repetitions of the characteristic signature of a crack within predetermined time windows to distinguish between data corresponding to a bona fide crack in the structural member from data produced by the effect of noise, dirt, grease, etc. upon the eddy current signal.

17 Claims, 11 Drawing Figures

Fig_4C

Fig_4D

METHOD AND APPARATUS FOR AUTOMATED INSPECTION OF FASTENER HOLES BY EDDY CURRENT

BACKGROUND OF THE INVENTION

This invention relates in general to the use of eddy currents for detecting discontinuities, and relates in particular to an automated system for detecting cracks or other discontinuities in the periphery of fastener holes and detecting noise conditions which may mask the detection of a crack.

The safe and efficient maintenance of aircraft is of vital concern to the air transporation industry and to the defense of the nation. Stress upon aircraft structural members produced by flying causes metal fatigue and often produces hairline cracks in such members which are difficult to detect and require costly repair, and which if uncorrected can result in disastrous failures and accidents.

The workpiece commonly involved in fastener hole inspection is an aircraft structural member which contains a number of holes drilled for fastening or mounting purposes. There is naturally a great interest in providing an efficient and effective method for inspecting these holes for structural defects and flaws which produces consistent results and minimizes human intervention, interpretation, and error. Commonly, when a metal part has been subjected to excessive stress, metal fatigue results in hairline cracks which emanate radially from the periphery of the hole. Moreover, even holes newly drilled in structural metal parts can have hairline cracks. These cracks are often extremely small and are not readily apparent to the unaided eye. Fastener holes in critical structural components such as airframe members must be 100% inspected for cracks, and the inspection task is often complicated by the inaccessibility of a hole for viewing and by the presence of dirt, grease, or noncritical surface imperfections which obscure the presence of a crack or give a false impression that a crack is present.

It has long been known that the introduction of a magnetic field of alternating magnitude in current-conducting materials induces eddy currents in these materials. These eddy currents are detectable by a probe which senses the magnetic field produced in turn by the flowing of the eddy currents. During World War II, techniques were devised whereby an eddy current was induced in the vicinity of a fastener hole, and the eddy current was detected by a probe and displayed on a meter which could be interpreted by a human operator. Variations in the conductivity, permeability, or physical characteristics of the material, including variations caused by cracks or similar physical anomalies in the material, cause changes in the induced eddy current. A skilled operator could often determine the existence of a crack in the workpiece by observing fluctuations of the induced eddy current. This approach is at best haphazard due to meter fluctuations caused by positioning the probe into the hole. Further problems are encountered when the hole contained imperfections such as dirt, an out of round condition, scratches or corrosion. These conditions produce "noise" in the eddy current signal which complicated interpretation by masking the existence of a crack or by providing a spurious indication of a crack. Often, the operator will misinterpret signals produced by imperfections insignificant to structural integrity, rather than a crack, so that parts which had no crack are needlessly rejected.

The prior art discloses that it is possible to make eddy current devices which can be compensated for the placement of the probe into the hole and for its removal from the hole. Devices with compensation circuits which correct for placement and removal of the probe have been in existence for a number of years. One such device is the Model ED-520 eddy current instrument manufactured by Magnaflux Corporation, Chicago, Ill. These prior art devices, however, are susceptible to noise in the signal due to an insufficiently cleaned hole, scratches, an out of round condition, etc.

Correction for elimination of noise has proven a difficult problem. A device for distinguishing flaw signals from various noise signals in eddy current instrumentation circuitry is disclosed in Downs, U.S. Pat. No. 4,193,028. This device purports to distinguish an eddy current signal produced by a crack from an eddy current signal caused by noise. This device is premised on the theory that an eddy current signal produced by crack is characterized by a waveform which exceeds a predetermined negative threshold voltage followed immediately by a predetermined positive threshold voltage. According to the system of the Downs patent, a noise signal will not give an indication that a crack exists because of the low probability that a noise signal will pass the predetermined negative voltage threshold followed within the requisite time by a voltage swing exceeding the predetermined positive threshold voltage.

A problem encountered in the device of Downs is that there are circumstances in which a noise signal falsely indicates it is a crack signal. In these circumstances, the noise signal will meet the criteria for constituting a crack signal because the voltage level exceeds the predetermined negative voltage followed within the requisite time by a voltage level exceeding the predetermined positive level. It is rare for this noise signal to repetitively give false indication that a crack exists; however, it is annoying, forces a repetition of the test, and creates a situation of uncertainty for the inspector who must exercise judgement based on possibly-spurious information.

A further problem encountered with the use of Downs' device is that it employs monostable multivibrators triggered by the output of a differentiator. These one shot multivibrators are susceptible to being triggered by spurious noise signals which approach but do not exceed the predetermined threshold. This susceptibility to false triggering may result in a diagnosis of cracks in the workpiece when in fact no cracks exist. The susceptibility to false triggering appears to be compounded in the Downs arrangement because the one shots are triggered by the output of a differentiator circuit.

It is also known in the art to use digital techniques to perform signal detection and measurement functions. Moreover, it has been possible to program general purpose digital computers to perform calculations and computations upon measurements obtained in this fashion. However, the prior art does not disclose either the use of digital circuitry and analysis or the use of computing devices to gather eddy current data for the purpose of performing crack signal analysis. Nor does the prior art disclose any apparatus designed to detect the repetition of crack signatures within predetermined time windows for the purpose of distinguishing crack signals from spurious and non-repetitive noise signals. The prior art also does not disclose the employment of digital signal analysis techniques to distinguish noise signals from crack signals by taking sufficient samples of data to ensure the statistical validity of crack data over noise data. Thus, prior art devices only detect the existence of one eddy current signal signature which may or may not constitute a valid crack signature in light of further inspection.

SUMMARY OF THE INVENTION

The present invention, stated in general terms, determines the existence of cracks in a workpiece by analyzing the effect of such cracks upon waveform signals representing eddy currents induced in the workpiece. In particular, the invention disclosed herein is an apparatus and a method for automating the inspection of fastener holes in a structural member for determining the existence of cracks in the vicinity of the hole. This invention provides an eddy current fastener hole inspector and crack detector apparatus which digitizes eddy current data obtained by the movement of an eddy current inducing probe in a hole in a workpiece, and analyses the data samples obtained from the probe over a predetermined amount of hole travel to determine whether a series of crack signals occurs within a predetermined time window. The invention also analyses the data samples for the occurrence of a predetermined number of noise peak signals which indicates an unacceptably noisy hole has been examined, rather than a valid crack found in such hole.

The microcomputerized eddy current fastener hole inspector and crack detector of the present invention identifies a characteristic signal produced by the presence of a crack in the vicinity of a hole in a workpiece, by establishing voltage and time relationships between sequential positive, negative, and positive excursions of the eddy current signals in order to distinguish such signals from noise.

This is accomplished by analyzing data acquired by an eddy current probe for the occurrence of signal excursions exceeding a predetermined threshold magnitude. A number of these signal excursions in excess of a predetermined number indicates the presence of an unacceptable noise level in the hole which might conceal the existence of a crack. Also during analysis the device seeks the detection of multiple valid crack signatures within predetermined time windows which indicates that a crack has been located in the workpiece. The invention provides a convenient automated method whereby an eddy current probe may be helically moved in a hole in a workpiece with minimal operator intervention and interpretation. Data produced by the gradual motion of the eddy current probes through a workpiece hole is digitized, accumulated, and analyzed. As a predetermined statistically valid number of data samples is being accummulated, a characteristic signal pattern corresponding to the existence of a crack in the workpiece is sought. Upon obtaining a predetermined number of these characteristic signal patterns, a crack in the workpiece has been verified, the operator of the device is automatically alerted, and a strip chart recording of the accumulated data is automatically printed. Upon the detection of the existence of unacceptable noise levels in the workpiece, the invention automatically cautions the operator, and prints a strip chart recording of the accumulated analyzed data.

It is an object of the present invention to provide an automated fastener hole inspection apparatus and method which minimizes operator intervention and interpretation.

It is a further object of the present invention to provide an automated fastener hole inspection apparatus and method which automatically inspects a fastener hole for cracks or discontinuities emanating from such hole and alerts or signals the operator upon the detection of same.

It is still a further object of the present invention to provide automated fastener hole inspection apparatus and method which automatically inspects a fastener hole, identifies the presence of noise resulting from dirt, scratches, corrosion, an out of round condition, and other conditions which might interfere with the detection of a crack signal emanating from such hole, and alerts or signals the operator that such conditions exist and warrant rectification before an inspection can accurately verify the presence or absence of a crack.

It is still a further object of the present invention to provide an automated fastener hole inspection apparatus and method which, upon detection of discontinuities in the vicinity of the hole or of noise conditions which might obscure the accurate detection of such discontinuities, automatically provides a strip chart recording of the data indicating that discontinuities or noisy conditions prevail.

It is still a further object of the present invention to provide an automated fastener hole inspection apparatus which employs highly fast and accurate digital signal processing techniques to gather and analyze data produced by an eddy current instrument and probe used in the inspection of such hole, and which employs techniques for ensuring that sufficient data samples are analyzed during such inspection to provide statistically valid indications that either discontinuities or noise conditions have been detected in the hole.

DETAILED DESCRIPTION OF PREFERRED EMBODIMENT

Figure 1:
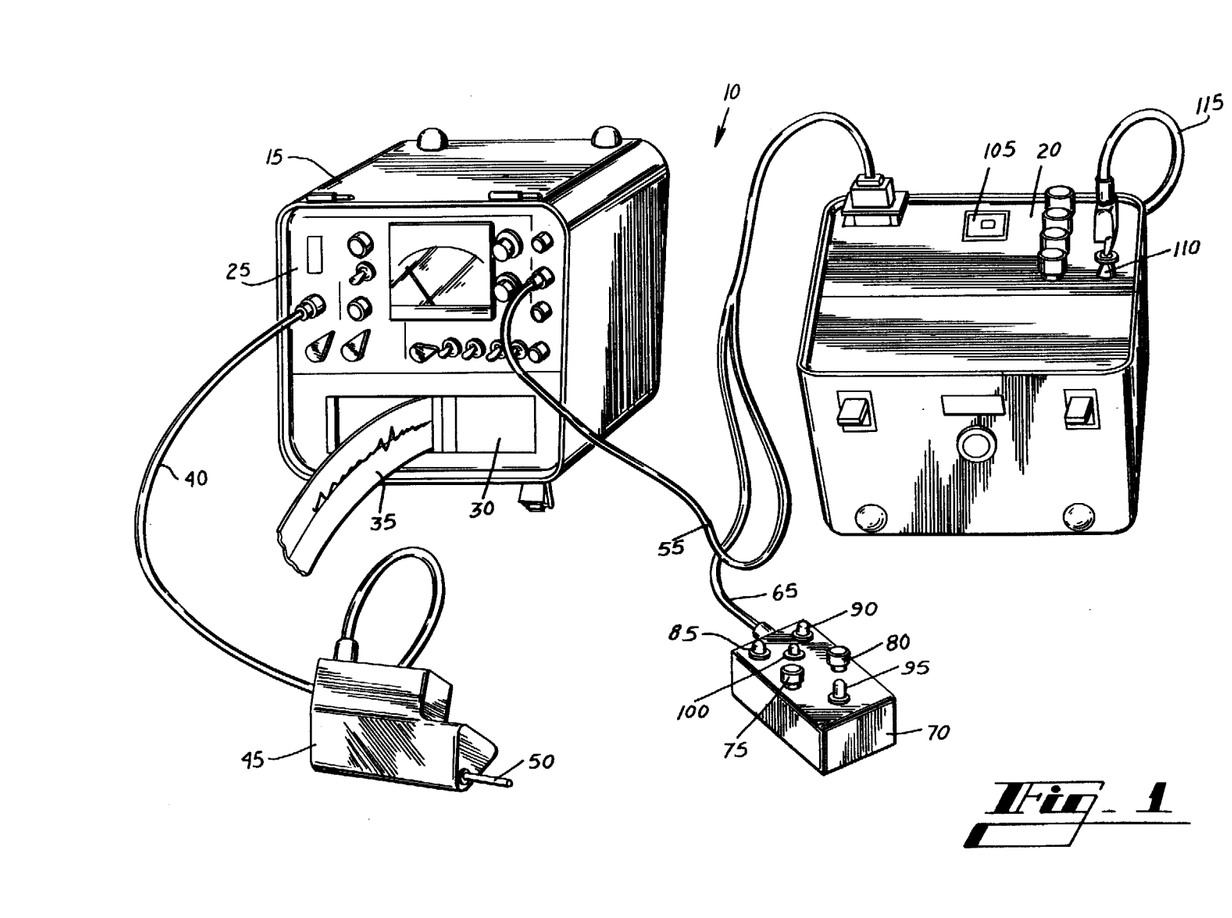
FIG. 1 is a pictorial view of a preferred embodiment of the present invention.

As can be seen in FIG. 1, the preferred embodiment comprises two major assemblies composed of an upper cabinet 15 and a lower cabinet 20, which may attach together to form a portable carrying case. The cabinets 15 and 20 each contain separate components of the system indicated generally at 10.

The cabinet 15 contains an eddy current instrument 25 such as the Model ED-520 manufactured by Magnaflux Corporation of Chicago, Ill., the face of which is exposed to view. Also contained in cabinet 15 is a strip chart recorder 30 which produces a strip chart recording 35 when appropriate. Emanating from the left side of cabinet 15 is a cable 40 which carries electrical power and control signals to the probe housing 45.

The probe housing 45 contains suitable electromechanical apparatus such as a motor and lead screw for advancing the probe 50 along a helical path into the hole under test. The probe 50 comprises a coil (not shown) which receives an alternating current signal from an oscillator in the eddy current instrument 25, and induces an eddy current in the material surrounding the hole under test. Signal generating and detecting apparatus in the eddy current instrument 25 senses eddy current changes or anomalies produced by cracks or variations in the material. Those skilled in the art will recognize the existence of well-known technologies for inducing and detecting eddy currents in workpiece holes.

A cable 55 connects cabinet 15 with cabinet 20. This cable supplies signals and power to cabinet 20 from cabinet 15, and carries data signals from the cabinet 20 to cabinet 15. Also emanating from the lower cabinet 20 is a cable 65 which carries power and control signals to an operator interface 70. The operator interface 70 contains a "run" button 75, a strip chart recorder activation or "print" button 80, a green "ready" light 85, a white "inspection in progress" light 90, an amber "noise caution" light 95, and a red "crack alarm" light 100. These lights are lit upon command by the apparatus under control of the microcomputer when appropriate.

The cabinet 20 also contains a thumb wheel switch 105, a power on-off switch 110, and a power connection 115 which allows the system to be connected to 110 volts A.C. power. The lower cabinet 20 further contains the signal processing apparatus set forth below in greater detail.

Figure 2:
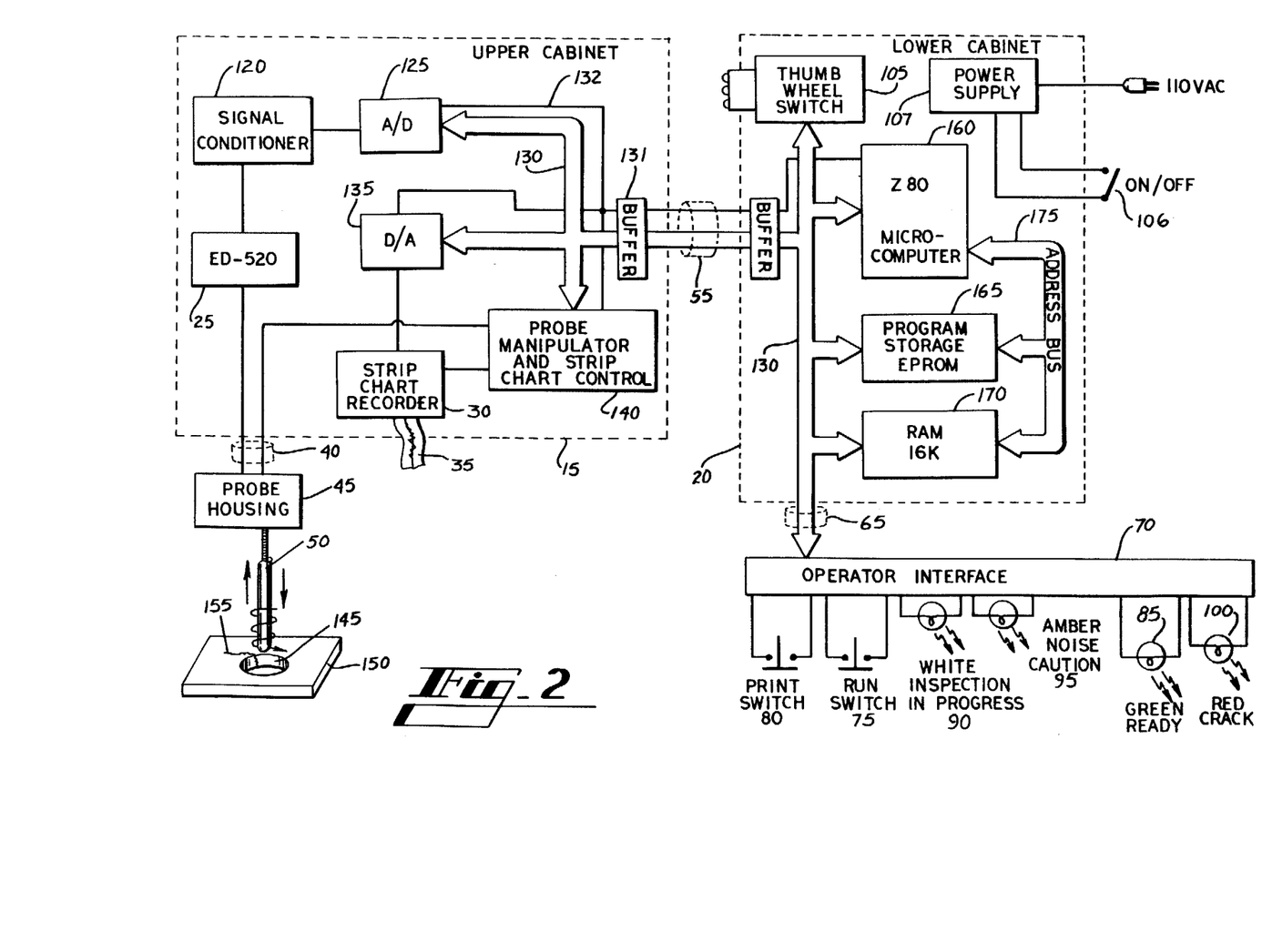
FIG. 2 is a block diagram of the preferred embodiment.

Referring to FIG. 2, it will be seen that the components of the disclosed embodiment are depicted within broken-line enclosures corresponding to cabinet 15, cabinet 20, and the operator interface 70. It will be understood, however, that the disclosed placement of a particular component in a designated cabinet is a matter of design selection and is not critical.

A signal conditioner 120, FIG. 2, prepares the signal received from the eddy current instrument 25 for reception by an analog to digital (A/D) converter 125. The A/D converter 125 transforms the analog signal from the signal conditioner 120 into a sequence of 8-bit digital words which are placed, upon receipt of an appropriate timing signal, into microcomputer 160 on bidirectional data bus 130 which serves as a data link between various components within the system. Data bus 130 is shown including a buffer 131 which drives and receives signals across cable 55 to cabinet 20. Control lines 132 which provide control signals to cabinet 15 components also emanate from buffer 131.

Also contained within cabinet 15 is a digital to analog converter (D/A), shown at 135 in FIG. 2, which receives digital information from the data bus 130 upon command and makes the information available in analog form to the strip chart recorder 30. Strip chart recorder 20 then reproduces an analog print-out of the information fed the converter 135 on data bus 130, upon receipt of appropriate control commands along control lines 132.

The probe manipulator and strip chart control circuitry, shown at 140 in FIG. 2, also receive digital data from the data bus 130 and control commands on control line 132. The data includes specific control signals for activation of the strip chart recorder 30 and the probe 50. The decoded commands for the probe 50 are transmitted through a cable 40 to the probe housing 45, which contains an electric motor and suitable drive mechanism for advancing the probe 50 helically along the longitudinal axis of the hole under examination.

Upon command, the probe 50 rotates and helically moves within a hole 145 in a workpiece 150, shown in FIG. 2. The probe 50 contains a coil (not shown) for inducing and detecting eddy currents in the workpiece 150. When the probe 50 has completed a predetermined number of revolutions and has moved a predetermined distance into the hole, the probe manipulator control 140 terminates the motion of the probe 50. The existence of a crack 155 in the workpiece 150 produces characteristic signatures in the eddy current signal detected by the eddy current instrument 25 and translated into digital form by A/D converter 125 for processing. The characteristic signatures of the signal produced by the eddy current instrument 25 upon the encounter of a crack will be described in further detail hereinbelow.

The cabinet 20 shown in FIG. 2 contains a thumb wheel switch 105, which is used to set the length or distance of hole inspection desired, and a power on/off switch 106 which is used to control electrical power from the power supply 107. It will be understood that power supply 107 can take various forms including A.C. power and rechargable batteries capable of recharging from A.C. power. Although not shown in FIG. 2, it will be further understood that power from power supply 107 is provided to all components of the system through well-known power cabling and bussing techniques.

Contained within cabinet 20 is a microcomputer 160 which in the preferred embodiment is a single card Z80 microcomputer circuit board manufactured by Cromemco, Inc. of Mountain View, Calif. This microcomputer 160 may instead be comprised of any of a number of microcomputer circuits which are currently available and familiar to those skilled in the art. The preferred embodiment employs the Z80 microcomputer chip set manufactured by Zilog Corporation of Cupertino, Calif. Associated with the particular microcomputer boards manufactured by Cromemco is program storage memory 165 which consists of erasable programmable read only memories (EPROM) and a sixteen kilo byte (16K) random access memory (RAM) 170 which stores digital information fed to it over the data bus 130 under control of the microcomputer 160. The program storage memory 165 and random access memory 170 are addressed by the microcomputer 160 along sixteen-bit address bus 175, which is capable of accessing 65K bytes of memory with its 16 lines.

Emanating from cabinet 20 is cable 65 which extends to the operator interface 70, shown functionally in FIG. 2. This operator interface 70 contains "print" switch 80 which serves as a strip chart recorder activation button, and "run" switch 75. The "run" switch 75 is used to signal the microcomputer 160 that the probe 50 has been located relevant to the hole to be inspected and that the system is to inspect the hole for cracks. The "print" switch 80 commands the microcomputer 160 to activate the strip chart recorder 30 to produce a strip chart recording 35 at the time the system has completed its examination of the hole. In the preferred embodiment, a strip chart recording is automatically provided whenever a crack or noise is encountered. Thus, the "print" button is used only to obtain a recording on a hole which the system has ascertained is free from cracks or noise, or to obtain a duplicate recording where a crack or noise was encountered.

Operator interface 70 also houses a number of status and signal lights, shown functionally in FIG. 2. When the system has been powered on and initialized and is ready to perform examination of a hole, a green "ready" light 85 is illuminated by the microcomputer 160. During the inspection of a hole, a white "inspection in progress" light 90 is illuminated. If the analysis of the data produced by the examination of the hole indicates noise which might mask the existence of a crack, the microcomputer activates an amber "noise caution" light 95. If, however, the microcomputer finds during analysis of the data that a crack exists in the workpiece, the microcomputer then illuminates the red "crack alarm" light 100.

Figure 3A:
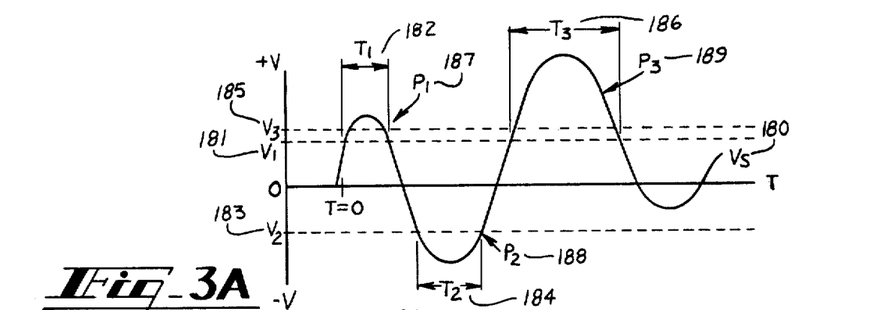
FIGS. 3A–3D are waveforms which display the time and voltage characteristics of the eddy current signal and the combinations of eddy current signals which are characteristic of the detection of the existence of a crack and the presence of unacceptable noise.

Reference is now made to FIGS. 3A-3D for an explanation of the timing and voltage characteristics of the signal produced by the eddy current instrument 25 which indicate the existence of a crack in the workpiece. FIG. 3A is a representative wave form produced by a crack signature in the workpiece as the probe approaches and passes the crack. Voltage $V_s$, shown at 180, represents the output produced by the eddy current instrument 25 prior to conversion into digital form for processing by the microcomputer 160. A crack typically will produce a characteristic signature in the eddy current instrument output which consists of three peaks: a positive sinusoidal peak, followed by a negative sinusoidal peak, followed by a positive sinusoidal peak. This characteristic signature voltage $V_s$ has been empirically determined to comprise a voltage excursion which exceeds a certain positive threshold voltage $V_1$, shown at 181, for a time period equal to or exceeding $T_1$, shown at 182, followed by a voltage excursion which exceeds a certain negative threshold voltage $V_2$, shown at 183, for a time period equal to or exceeding $T_2$, shown at 184, followed by a voltage excursion which exceeds a certain positive voltage threshold voltage $V_3$, shown at 185, for a time period equal to or exceeding $T_3$, shown at 186. It has also been empirically observed that the values of $V_1$ and $V_3$ are approximately 0.4 volts and voltage $V_2$ is approximately $-0.7$ volts, in a specific embodiment of the present invention.

The time characteristics of the eddy current voltage $V_s$ are defined in terms of the rotation rate of the probe 50 within the subject hole. The eddy current probe rotates within the hole under inspection, producing the analog waveform of voltage $V_s$ having a timebase T corresponding to the angular velocity of the probe within the hole. The analog signal provided by the eddy current instrument 25 is digitized by dividing the waveform into 200 points equally spaced about each revolution of the probe within the hole. To ensure a statistically valid indication that a crack has been detected, sufficient data points or samples are required, both above and below certain threshold levels, and within certain sequential data point limits or probe revolutions as discussed hereinafter.

The time period of the characteristic signature of the crack signal may be defined in terms of the number of consecutive sample points at which the analog voltage $V_s$ exceeds the threshold voltages defined above. Time $T_1$ has been observed to equal or exceed five consecutive data points; time $T_2$ has been observed to equal or exceed seven consecutive data points; and time $T_3$ has been observed to equal or exceed twelve consecutive data points.

Also, a second time period for the characteristic signature of the crack signal is involved, which may be defined in terms of the number of consecutive sample points of the analog voltage $V_s$. This second time period consideration concerns the time spacings between parameters of time pair $T_1$ and $T_2$ and time pair $T_2$ and $T_3$.

Since the analog to digital conversion arrangement of the preferred embodiment samples waveform $V_s$ a predetermined number of times per revolution of probe 50, it will be appreciated that the numbers and timing of data samples described above correspond to predetermined segments of angular displacement of probe 50.

The preferred embodiment of the invention recognizes the characteristic signature produced by a crack only if the voltage excursions exceed the above-identified predetermined threshold voltages for the indicated predetermined number of data points and within the time constraints of predetermined numbers of consecutive data points, i.e., a positive peak $P_1$, shown at 187, with at least five consecutive data points above threshold $V_1$; followed by a negative peak $P_2$, shown at 188, with at least seven consecutive data points below threshold $V_2$, but within such time that the seventh data point of $P_2$ below threshold $V_2$ occurs within 60 or fewer consecutive data points after the fifth data point of $P_1$ has occurred; followed by a positive peak $P_3$, shown at 189, with at least twelve consecutive data points above threshold $V_3$, but within such time that the twelfth data point of $P_3$ above threshold $V_3$ occurs within 45 or fewer consecutive data points after the seventh point of $P_2$ has occurred. Thus, the detection of peak $P_1$ starts timing windows for peaks $P_2$ and $P_3$, which if detected provide a crack "signature".

In order for the "crack alarm" light to be lit, the preferred embodiment must find that a multiple series of at least three crack signatures, or nine total peaks, have been recognized within a window of less than 600 data points. In other words, the device must detect the cracks's characteristic signature once upon each of three contiguous rotations of the probe within the hole. It will be observed that many more than three revolutions of the probe can occur within any given hole, as the probe advances along a helical path. Thus, it will be appreciated that the rate of probe advance along the axis of a hole must be chosen with reference to the rate of probe rotation so that the effective detection range of the probe will pass proximate any given point upon the hole surface boundary at least three times. This ensures that the requisite minimum of less than 600 data points can be considered as the probe advances past a crack, i.e., the probe's effective detection area must pass over or proximate a crack at least three times before sufficient data have been considered to find a crack. Consequently, data corresponding to three complete crack signatures must be encountered within the window of less than 600 data points provided by three probe revolutions to trigger a "crack alarm".

Figure 3B:
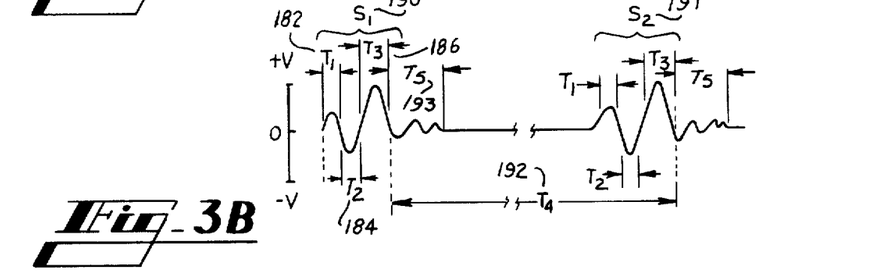

Referring now to FIG. 3B, two of these characteristic signatures are shown, it being understood that the preferred embodiment actually looks for three. Two consecutive signatures, $S_1$, shown at 190, and $S_2$, shown at 191, are depicted. If the voltage has exceeded the threshold $V_3$ for time $T_3$ (i.e., a peak $P_3$ of a crack signature like the one in FIG. 3A has been observed), crack signature $S_1$ is established and a time period $T_4$, shown at 192 in FIG. 3B is begun to be measured. Thus, as the signature threshold voltages and number of time point tests are satisfied, thereby producing an indication that one complete crack signature $S_1$ has occurred, the system looks for the occurrence of a second complete signature $S_2$ within the time period $T_4$. The measurement of time period $T_4$ begins when the voltage threshold $V_3$ is exceeded for the twelfth occurrence during time period $T_3$, i.e., when peak $P_3$ is found.

In the preferred embodiment, time $T_4$ is considered to equal 220 data points. By taking the two hundred data points for one complete revolution, and adding consideration for possible additional data points for assurance purposes, it can be appreciated that an outside limit of 220 data points for time period $T_4$ within which a subsequent characteristic signature is expected if in fact a real crack has been encountered is reasonable.

The existence of the third peak $P_3$ of an actual signature ($S_1$ or $S_2$) triggers the start of the timing window $T_4$. Thereafter, if there truly exists a valid crack signature, the subsequent signature $S_2$ or $S_3$ follow within a fixed time. The timing window $T_4$ of 220 data points after the completion of the first crack signature $S_1$, shown at 190 in FIG. 3B, and the rotation of the probe throughout 360° which generates an additional 200 data points, allows sufficient time within which there must occur another crack signature $S_2$, shown at 191, comprised of its own peaks $P_1$, $P_2$, and $P_3$. If and only if the subsequent crack signature is completed within the requisite time window $T_4$ will the preferred embodiment acknowledge that a valid potential crack signal has been recognized in the case of $S_2$ occurring within time period $T_4$ after $S_1$, or that an actual valid crack signal has been recognized in the case of the requisite $S_3$ occurring within time period $T_4$ after $S_2$.

Since the $V_s$ values for both $P_1$ and $P_3$ are positive, and in recognition that the quantity of sequential data points in $P_3$ above threshold $V_3$ may exceed the minimal amount of twelve with such surplus data points above threshold $V_1$, a safeguard logic may be desired or included in the data point crack analysis routine to preclude the appearance of a subsequent $P_1$ from what is in fact excess or surplus data points from the already detected $P_3$. Such safeguard could be included in the preferred embodiment under discussion by the provision of an additional time window $T_5$ shown at 193 in FIG. 3B during which a predetermined quantity of sequential data points immediately following establishment of $P_3$ are still counted but ignored or overlooked in the crack analysis routine before a subsequent $P_1$ can be indicated. Such time window $T_5$, when included, should be long enough to preclude a false indication of a subsequent $P_1$ yet not too long to preclude an actual subsequent $P_1$, and is preferably in the range of from approximately 25 to approximately 75 consecutive sequential data points after establishment or recognition of a $P_3$. It is also to be noted that any omission or by-pass of window $T_5$ data points from crack analysis does not preclude noise analysis of such data points, as discussed in more detail hereinafter.

Figure 3C:
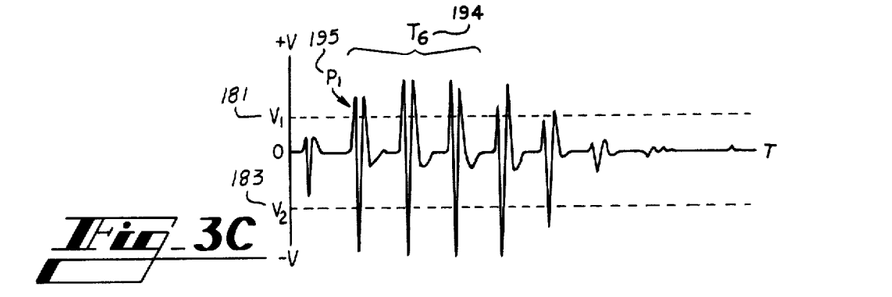

In summary, there must appear at least a total of three crack signatures (nine total peaks) within less than three complete revolutions of the probe in the hole for the device to acknowledge the existence of a crack and light the "crack alarm" light. It may be appreciated that requiring multiple occurrences of crack signatures ensures that a statistically relevant sample of data has been taken so as to distinguish a real crack from one or even two occurrences of noise which have waveforms similar to crack signatures. This arrangement of the preferred embodiment leads to increased reliability of the crack detector and eliminates reliance upon operator judgment. It will also be apparent to those skilled in the art that this arrangement will not give false crack signals of the type which may be generated by the Down apparatus noted hereinabove in response to a noise signal which resembles a portion of one crack signature. In FIG. 3C, the pattern of nine total peaks (or three crack signatures), within the time window $T_6$ of less than 600 data points shown at 194, triggered by peak $P_1$ at 195, may be seen.

Figure 3D:
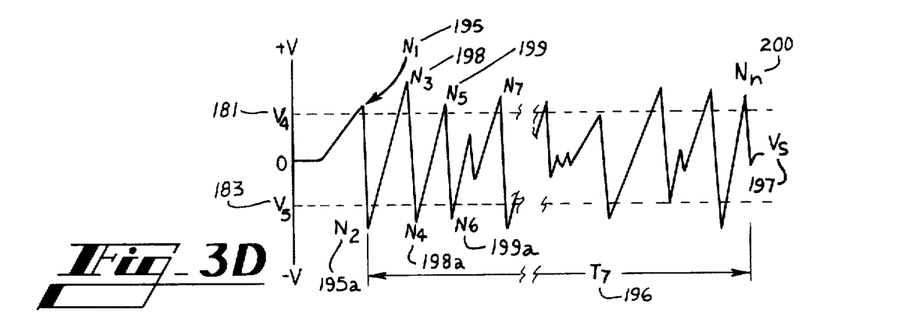

The preferred embodiment of the present invention alerts the operator if noise signals of large magnitude which might mask the existence of a crack in the workpiece are detected in the hole under inspection. In the event that the eddy current signal $V_s$, after signal conditioning and filtering, produces a "noisy" waveform, the preferred embodiment will light the "noise caution" light and automatically provide a strip chart print-out of the data obtained by the probe. FIG. 3D shows such a noisy waveform $V_s$.

In FIG. 3D, it can be seen that the presence of a peak $N_1$, shown at 195, above threshold $V_4$ is located within a timing window $T_7$, shown at 196, which consists of a moving array of the 600 most immediate preceding and sequential data points to the one currently being analyzed whereby the correct count for noise peaks in the continuous moving time window of 600 data points or three probe revolutions may be monitored. The signal $V_s$, shown at 197, is that of a noise signal rather than that of a valid crack signal although it is to be recognized that noise signal 197 may be of sufficient shape and magnitude to mask a valid crack signal. It will be noted in FIG. 3D that peaks $N_3$ at 198, $N_5$ at 199, through $N_n$ at 200, exceed the positive threshold voltage $V_4$, shown at 181 and that peaks $N_2$ at 195a, $N_4$ at 198a, $N_6$ at 199a through $N_m$ at 200a, exceed the negative threshold voltage $V_5$ shown at 183. It has been determined that within the time period $T_6$ of three probe revolutions there must be at least three occurrences of a crack signature, which constitute a total of nine peaks minimum, for there to be a valid crack. Consequently, if a predetermined number of peaks are counted within the time period $T_7$ without meeting the proper sequencing and time constraints of a valid crack signal, the "crack alarm" 100 light will not be illuminated but rather the "noise caution" 95 light will belit. This feature of peak counting insures that the crack alarm is lit when sufficient and properly sequenced and timed crack peaks occur which exceed the crack threshold voltages. If a sufficient quantity of noise peaks are counted, the device also recognizes that conditions in the workpiece hole are such that the signal produced by the probe repeatedly exceeds the noise threshold voltage to indicate conditions which might mask the existence of a crack in the workpiece.

Consequently, the "noise caution" light 95 is illuminated, which advises the operator that attention must be paid to the workpiece hole before he can determine whether or not a crack indeed exists. These conditions can include the accumulation of dirt, paint, oil, scratches or gouges, an out-of-round condition, etc. After the hole has been corrected for these conditions, a re-examination of the workpiece hole may be made.

In order to use the preferred embodiment disclosed herein, the operator first switches on the "power on" switch 106. When the system is ready to inspect a hole, the green "ready" light 85 will come on. The operator then selects on thumbwheel switch 105 the depth of the hole to be inspected, and places the probe 50 in the hole so that the probe housing 45 is stationary and stable. The operator then presses the "run" button 75, on the operator interface 70. The "ready" light 85 will go off, and the white "inspection in progress" light 90 will come on. The probe will then automatically travel in the hole, and the system will process the data produced by the eddy current instrument 25.

If the system encounters a crack during the inspection, the red "crack alarm" light 100 will come on, and the strip chart recorder 30 will automatically produce a print-out 35 of the accumulated data for the operator to examine. Likewise, if the system encounters conditions which might mask the presence of a crack, the amber "noise caution" light 95 will come on and again a strip chart recording will be automatically produced. The "noise caution" light alerts the operator that attention must be paid to the hole before a proper inspection can be had. The operator can repeat the inspection after the noise conditions in the hole have been rectified.

In the event that neither the "crack alarm" or the "noise caution" light has come on, the operator may safely conclude that no cracks exist in the vicinity of the hole. If the operator chooses, he may then depress the "print" button 80 and the system will produce a strip chart recording of the data corresponding to the hole inspected. It may thus be appreciated that the preferred embodiment can prevent the unnecessary use and waste of strip chart recorder paper when the analysis does not reveal a crack or noise.

It is to be noted that each complete hole inspection by this device can result in one of four indications: i.e., a clear signal with neither noise nor crack; a crack alarm; a noise caution signal; or both crack alarm and noise caution signals.

FIGS. 4A-4E show a flow diagram which charts the steps taken by the microcomputer employed in the preferred embodiment shown in FIG. 1 in the examination of a workpiece hole and analysis of the data processed for crack signatures. Entering the diagram on FIG. 4A at the top of the page, in the START block 201, it will be seen that the first step taken by the microcomputer is to clear all flags, to turn off the probe manipulator and the strip recorder, and to illuminate the "ready" light 205.

Figure 4A:
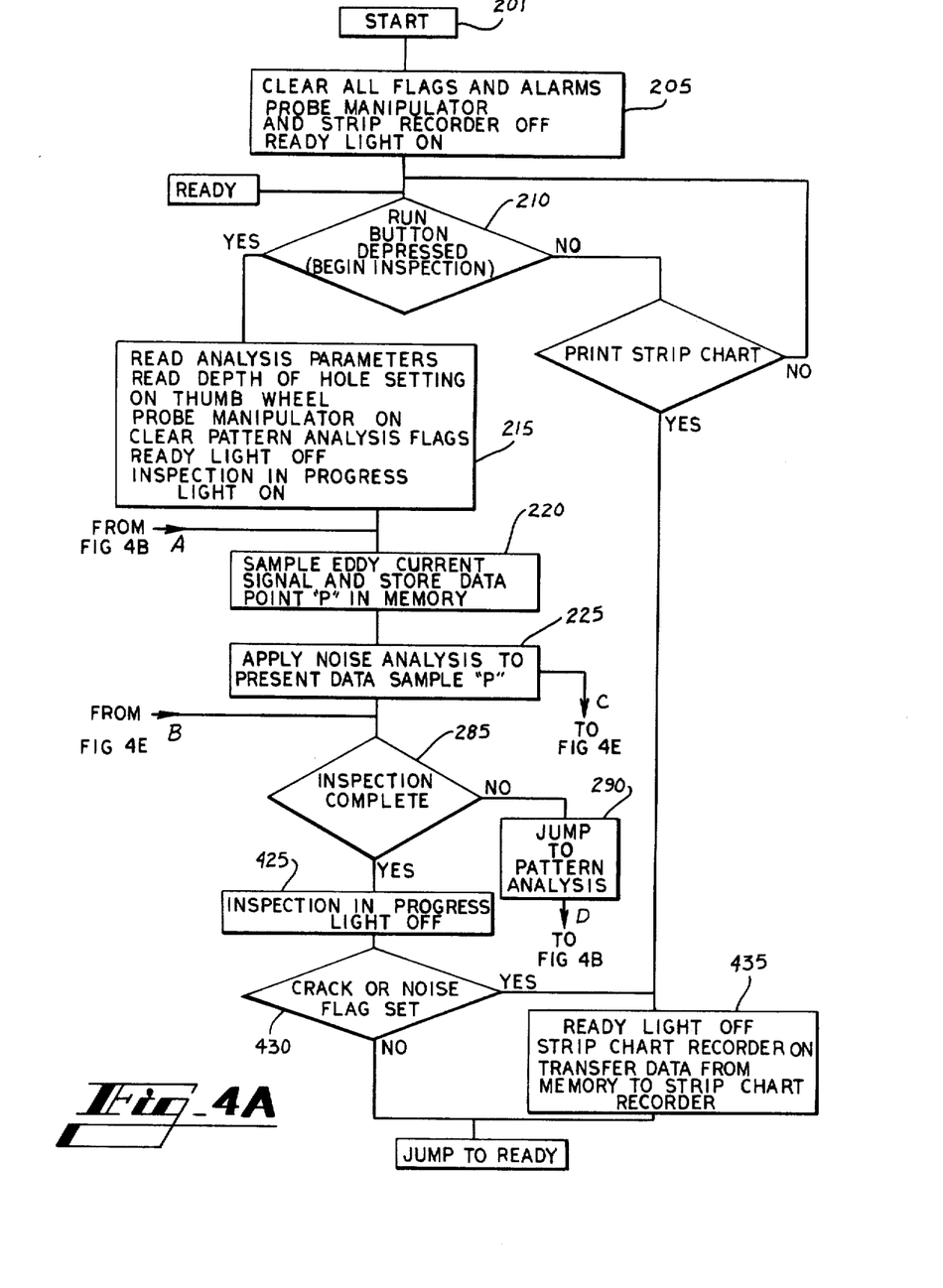
FIGS. 4A–4E are flow diagrams representative of the process whereby the preferred embodiment of the present invention initializes the eddy current probe, collects and analyses the resultant data from the probe, and provides an output indication of the existence of cracks or noise within the hole.

After these initializing steps are taken, the microcomputer polls the "run" switch to determine if it has been depressed. When the depression of this switch has been detected at 210, the microcomputer performs preliminary functions at step 215 including: determining the analysis parameters (voltage thresholds which have been stored in memory), reading the depth-of-hole inspection setting from the thumbwheel switch 105 (which results in establishing the number of data points to be analyzed), activating the probe manipulator (causing the probe to travel in the hole), instructing the eddy current instrument 25 to induce eddy currents in the workpiece, extinguishing the "ready" lamp 85, and lighting the white "inspection in progress" light 90.

As the probe 50 travels in the hole, the eddy current signal $V_s$ is produced by the eddy current instrument 25. The A/D converter 125 converts this signal $V_s$ into digital form at the rate of 200 eight-bit data samples, or points P, per revolution and places the data samples upon the bidirectional data bus 130, to be retrieved by the microcomputer 160 and placed in RAM 170. These steps are shown at 220.

The following symbols will provide a shorthand notation for certain references used in the discussion:

P—the value of the *present* data point being analyzed.
P-1—the value of the data point preceding the present point P.
GUF—"gone up flag", an indicator that a postive-going slope has been detected.
NMT—noise magnitude threshold.
NPC—noise peaks counter.
NPT—noise peaks threshold number.
PS—previous status flag.

After a data point is placed in memory, the NOISE ANALYSIS procedure shown at 225 is applied to the data point. The steps of the preferred NOISE ANALYSIS procedure are shown more particularly in FIG. 4E. First the magnitude of each data sample P is converted from the digital sinusoidal values of $V_s$ to an absolute value at 226 and then compared to the magnitude of the previous data sample P-1 at 227; when the magnitude of a data point P exceeds the magnitude of the previous data point P-1, the flag GUF is raised at 230. GUF, the "gone-up flag", is an indicator that a positive-going slope in the absolute value waveform of $V_s$ has been detected.

Figure 4B:
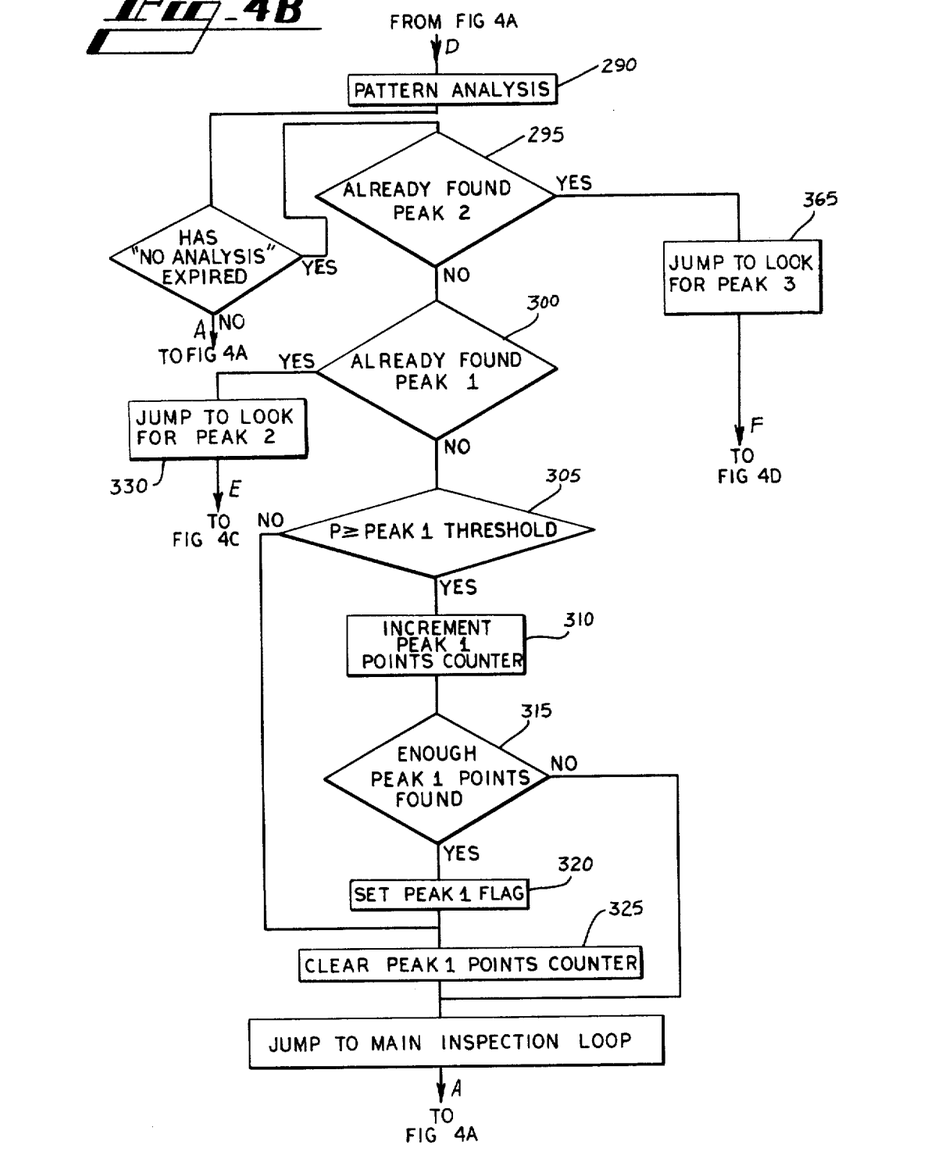
Figure 4C:
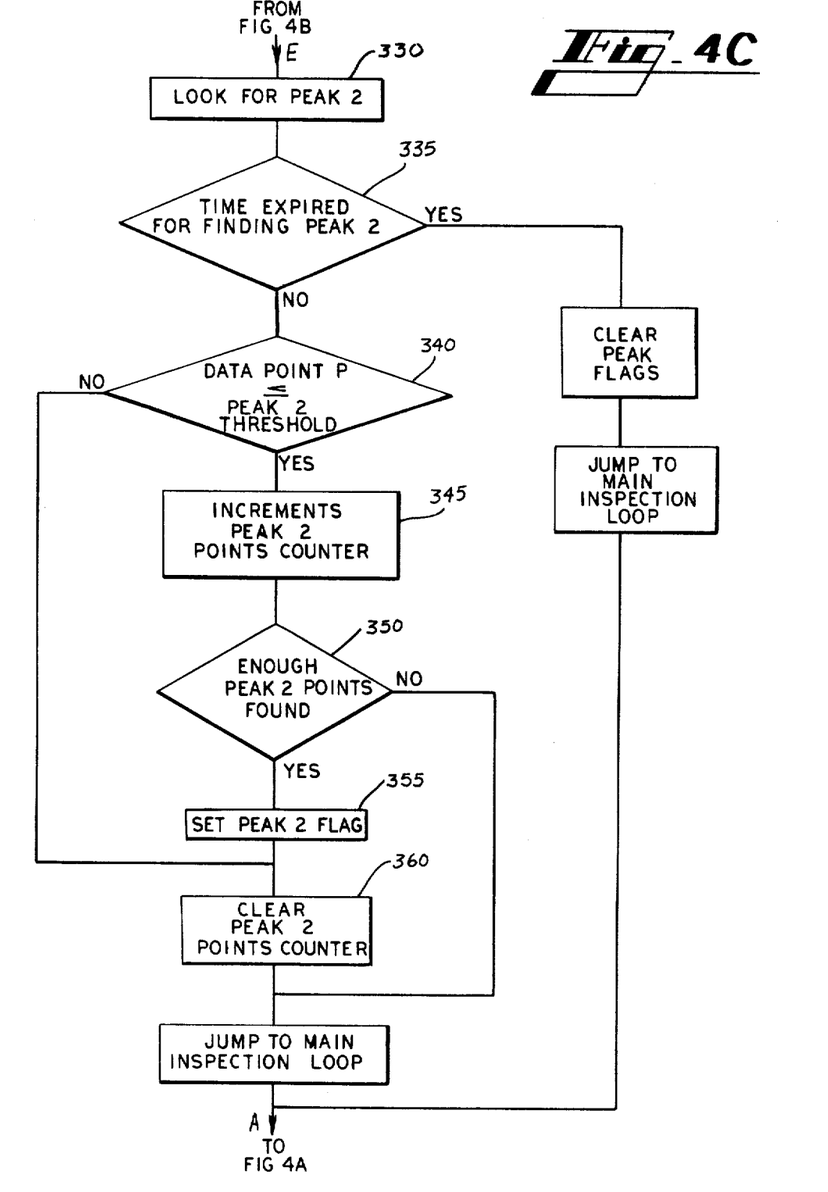
Figure 4D:
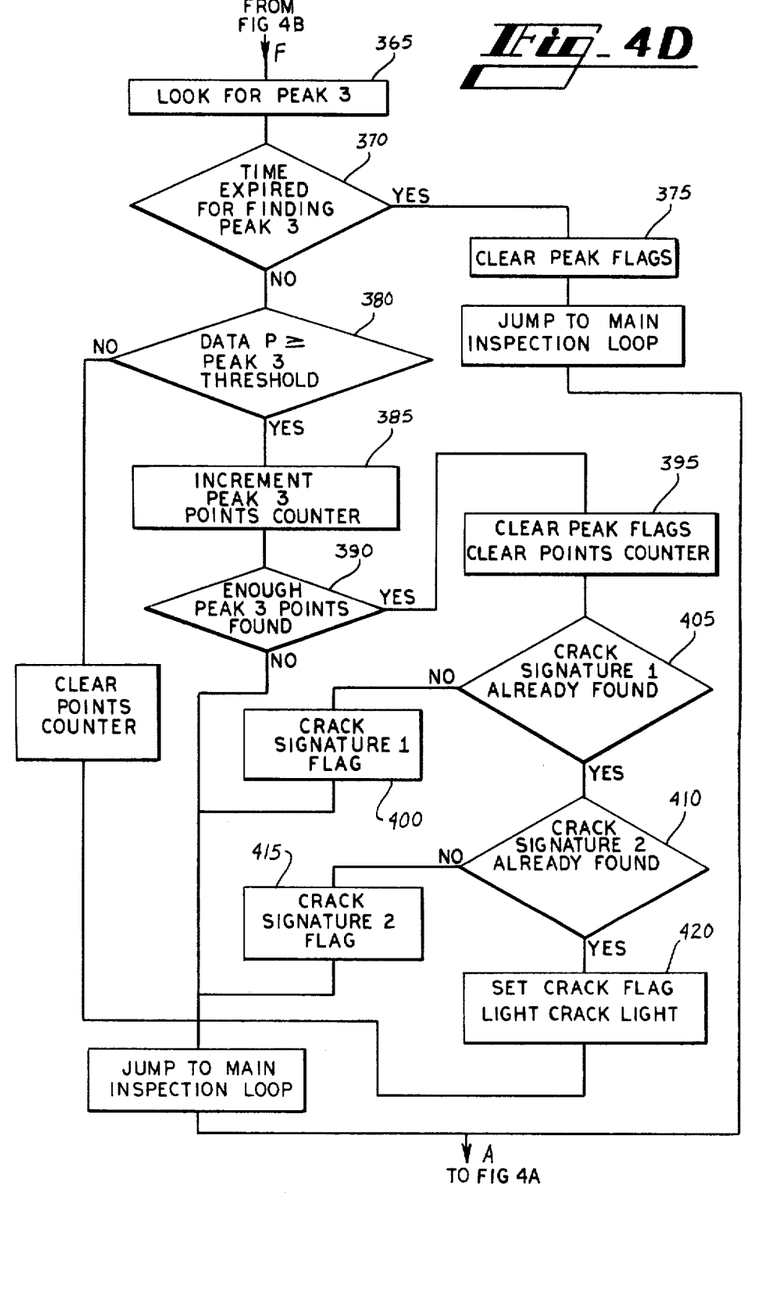
Figure 4E:
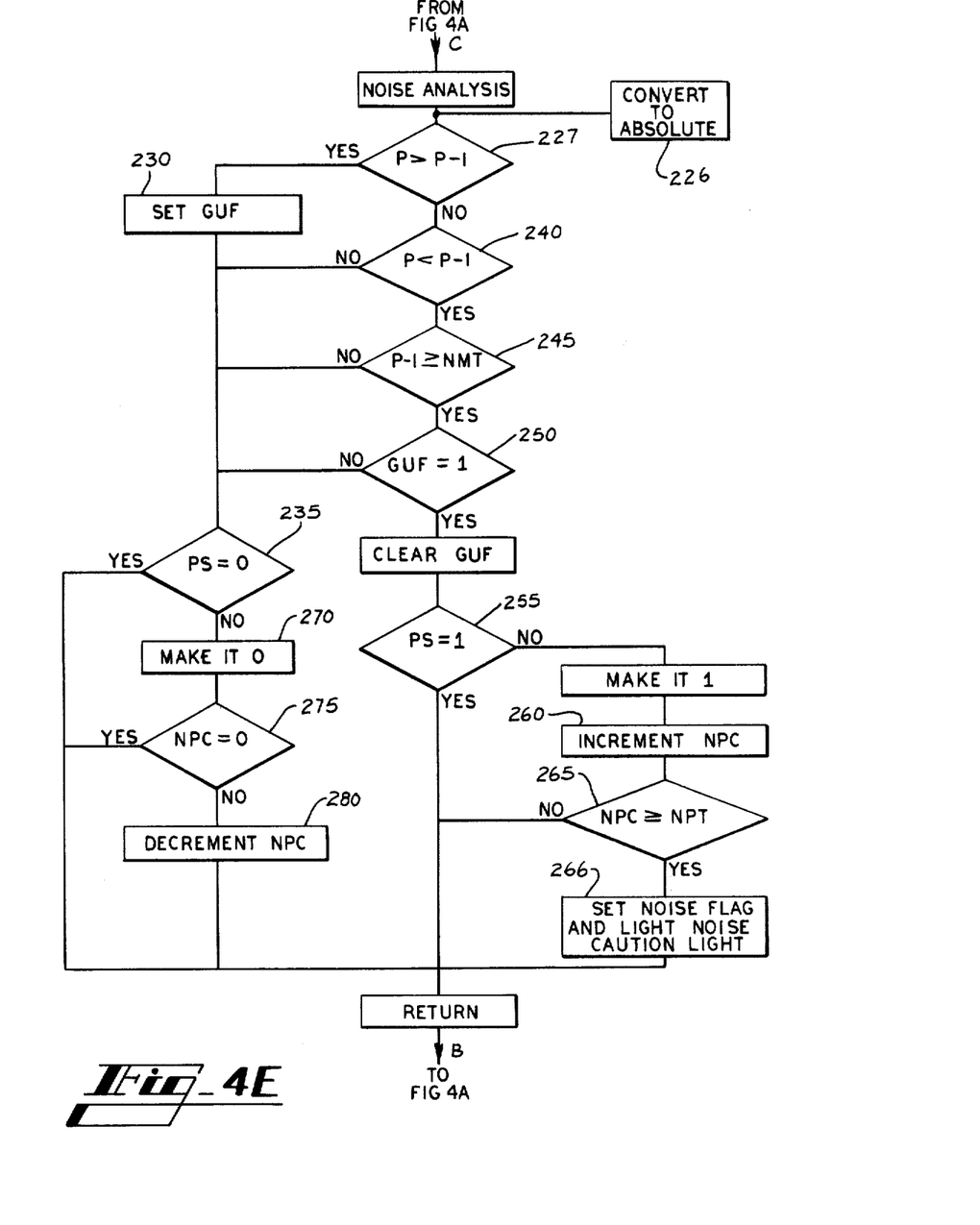

At decision block 235, FIG. 4E, the PS flag (previous status) is examined to determine its state. This PS flag indicates whether the first data point within the current noise time window $T_7$ has produced a noise peak or not, which in the described preferred embodiment is the 600th data point preceding the current one under analysis. Assuming that the previous status flag equals zero, the NOISE ANALYSIS subroutine will return to point B on FIG. 4A. However, for purposes of the following discussion, it should be noted on FIG. 4A that the preferred embodiment receives each data point, applies the NOISE ANALYSIS procedure on FIG. 4E, determines if the inspection is complete at 285, applies the PATTERN ANALYSIS procedure shown in FIG. 4B, and then returns to point A on FIG. 4A to analyze another data point P in the eddy current signal and store it in memory. The process is then repeated in the described embodiment 200 times per complete revolution of probe 50 in the hole so that such data point is received and analyzed for the inspection analysis.

Assume for purposes of discussion of the preferred NOISE ANALYSIS procedure that the next data point has been received and that NOISE ANALYSIS is being applied to the such next data point. With the foregoing assumption in mind, the NOISE ANALYSIS procedure shown on FIG. 4E first seeks to determine if there is a positive-going slope. As long as a positive-going slope is detected at 227, GUF will remain set at 230. At such time as data point P has a magnitude less than the previous data point P-1 at 240, a different test will be employed to determine if the data point P-1 exceeds a predetemined noise magnitude threshold (NMT) at 245, which in the preferred embodiment is in the order of 1 volt, which in turn means the values of $V_4$ and $V_5$ in FIG. 3D are $+1.0$ volts and $-1.0$ volts, respectively. In the event that the test at 245 is satisfied, and the data point P-1 exceeds NMT, the decision block 250 is entered which determines if GUF has been set. If this test is satisfied, all tests are satisfied for indicating that a peak in the signal has been reaches, so that the next step is decision block 255. It is at this point that the previous status (PS) flag is examined at 255.

It will be recalled that PS indicates whether or not a noise peak was found at the 600th data point preceding the one being analyzed, and which is the data point moving out of time window $T_7$ to be replaced by the current data point. Thusly, if PS is a logical one, which means the noise peak status established at the 600th data point preceding the current data point being analyzed will move out of time window $T_7$ and be replaced by the noise peak status established by the current data point being analyzed. Since the net result in this occurrence is merely a substitution of the earliest noise peak for the latest one entering into the moving point status array or time window $T_7$, the NOISE ANALYSIS subroutine will return to point B in FIG. 4A with the indication of PS-1 status of the current data point for movement through the array of time window $T_7$. On the other hand, if PS is a logical zero at 255 for the current data point under analysis, which indicates a noise peak, the PS for that point is set to a one and the noise peaks countr (NPC) is incremented by one at 260.

After the noise peaks counter is incremented at 260 it is compared to a predetermined number of noise peaks, the noise peaks threshold number (NPT) at 265 which in the preferred embodiment is a quantity of fifteen noise peaks of any combination of positive and negative peaks within the immediate preceding 600 data point window. If a sufficient number of noise peaks have been counted in the NOISE ANALYSIS procedure, the NOISE flag is set and the amber "noise caution" lamp is lit at 266 and control passes back to point B in FIG. 4A.

The NOISE ANALYSIS subroutine also provides PS logic whereby if the current data point is not indicative of a noise peak and the PS status of the 600th preceding data point about to pass out of the moving array covered by time window $T_7$ is a logical one, such noise peak is removed from the Noise Peak Counter. In this regard, any data point being analyzed that is not indicative of a noise peak will encounter decision block 235. As stated previously, if PS is zero, the NOISE ANALYSIS routine returns to point B in FIG. 4A. On the other hand, if PS is found to be a logical one at 235, the PS status for the current data point is made zero at 270 followed by a test of the NPC at 275. If NPC is a zero at this point in time, a return to point B in FIG. 4A is accomplished, whereas if NPC is anything other than zero (which will always be a positive integer), NPC will be decremented at 280 to remove the noise peak represented by the data point status passing out of the 600 data point array before return to point B in FIG. 4A.

Regardless of whether or not the NOISE ANALYSIS has resulted in the setting of the "noise caution" lamp, control will return to point B on FIG. 4A. At decision block 285 the inquiry is made as to whether the inspection of the hole is complete, i.e., whether all data points have been obtained and contained in memory. In the event that the inspection is not complete, decision block 285 passes control to PATTERN ANALYSIS at 290.

Referring now to point D on FIG. 4B, the preferred PATTERN ANALYSIS procedure may be examined. The microcomputer inquiries at 294 as to the expiration of any "No Analysis" period of time window $T_5$ (as described above) that may be included immediately after the establishment of a third peak $P_3$. If such time has not expired, control passes to point A in FIG. 4A, whereas if the current data point being analyzed is not within or not concerned with any crack analysis bypass, the microcomputer inquiry passes to 295 to determine whether PEAK 2 has been found, i.e., whether the existence of a second, negative-going peak $P_2$ within a characteristic crack signature has been detected. Assuming, since this is the first pass of this procedure, that $P_2$ has not been found, and also that $P_1$ has not been found at 300, the microcomputer inquires at 305 as to whether the data point P under examination exceeds a predetermined PEAK 1 threshold. In the preferred embodiment the PEAK 1 threshold equals a positive 0.4 volts. In the event that this test is satisfied, a counter which keeps track of the number of data points which exceed the PEAK 1 threshold is incremented at 310. The microcomputer next inquires as to whether a sufficient number of PEAK 1 points have been found at 315. In the event that an insufficient number of PEAK 1 points have been found, return is made to point A on FIG. 4A and another data point P is received and stored in memory. In the event that a sufficient number of PEAK 1 points have been counted by the PEAK 1 points counter at 315, five in the preferred embodiment, the PEAK 1 flag is set at 320, the PEAK 1 points counter is cleared at 325, and a return is made to point A on FIG. 4A. Again, another sample is taken of the eddy current signal and the representative digital data point P is stored in memory.

Assume now that the PATTERN ANALYSIS procedure on FIG. 4B has set the PEAK 1 at flag 320, indicating that the first peak $P_1$ of a characteristic crack signature has been found. Then, when PATTERN ANALYSIS returns to point D on FIG. 4B after the next data sample, LOOK FOR PEAK 2 will be the next step at 330, and control passes to point E on FIG. 4C. FIG. 4C outlines the path taken by the microcomputer after the first peak $P_1$ has been found. It should be recalled from the discussion above that the establishment of the first peak $P_1$ begins a timing by the microcomputer which establishes a window of 60 consecutive data points within which a second peak $P_2$ (which constitutes a negative-going peak) must be found followed by a third peak $P_3$ within 45 consecutive data points after $P_2$ in order for a valid crack signature to be detected. It will be further recalled that the establishment of each of $S_1$ and $S_2$ begins the 220 data point timing window $T_4$ within which the next of three validly established crack signatures must occur for the system to acknowledge that a crack has been found by illuminating the "crack alarm" lamp.

Assuming that the time for finding $P_2$ has not expired so that the "no" branch is taken from step 335, the data point P is examined to determine whether it is a negative voltage less than or equal to the PEAK 2 threshold as shown at 340, which in the preferred embodiment is $-0.7$ volts. In the event that the data point satisfies the threshold test, the PEAK 2 points counter is incremented at 345 and the microcomputer inquires whether a sufficient number of PEAK 2 points have been found to establish a negative-going peak $P_2$ at step 350. It may be recalled that the preferred embodiment seeks seven consecutive negative polarity data points above the PEAK 2 threshold magnitude to constitute a second peak. If the requisite number is found, the PEAK 2 flag is set at 355, the PEAK 2 points counter is cleared at 360, and control passes back to the main inspection loop at point A on FIG. 4A, which receives the next data point P and stores it in memory.

Assuming now that a first peak $P_1$ has been established on FIG. 4B, and a second peak $P_2$ has been established on FIG. 4C, it may be seen that control will be passed from FIG. 4B to LOOK FOR PEAK 3 at step 365, point F on FIG. 4D. As was required for $P_2$, the establishment of $P_1$ began a timing window of 45 consecutive data points following establishment of $P_2$ within which a third peak $P_3$ (of positive polarity) must be found in order for a valid crack signature to exist. The microcomputer inquires on FIG. 4D as to whether the time has expired for finding $P_3$ at 370. In the event that this time has expired, all peak flags are cleared at 375 and control passes back to point A on FIG. 4A. In the event that the time has not expired for finding $P_3$ at 370, an inquiry is made as to whether the data point P exceeds the PEAK 3 threshold at 380. As stated earlier, the PEAK 3 threshold in the preferred embodiment has been set at positive value of 0.4 volts, which happens to be identical to the PEAK 1 threshold.

In the event that the data point P exceeds the PEAK 3 threshold, the PEAK 3 points counter is incremented at 385 on FIG. 4D. Then, the microcomputer must determine whether enough PEAK 3 points have been found to establish the existence of a third peak $P_3$ and thus a crack signature. Also as stated earlier, the preferred embodiment requires that twelve consecutive data points exceeding the PEAK 3 threshold must be found in order for the microcomputer to establish that the third peak $P_3$ has indeed been established. In the event that an insufficient number of PEAK 3 points are found at 390, control passes to the main inspection loop on FIG. 4A and the next data point received by the microcomputer begins the analysis anew.

However, in the event that a sufficient number of PEAK 3 points have been established at 390, a crack signature has occurred in its entirety and the appropriate signals indicating the existence of this crack signature must be recorded. All peak flags are cleared and all point counters are reset to zero at 395. If this is the first crack signature to be established, the CRACK SIGNATURE 1 flag is set at 400, and control passes to the main program at point A on FIG. 4A.

If CRACK SIGNATURE 1 has previously been established when block 405 is reached on FIG. 4D, then inquiry is made as to whether CRACK SIGNATURE 2 has been established at 410. If not, the CRACK SIGNATURE 2 flag is set at 415 to record the encounter of this second crack signature.

In the event that CRACK SIGNATURE 1 and CRACK SIGNATURE 2 have been detected at step 410 on FIG. 4D, the point has been reached at which the detection of the third peak $P_3$ signifies that this is the third peak of the third crack signature, and therefore all the requirements for the existence of a crack have been established. Correspondingly, the CRACK FLAG is set, the "crack alarm" lamp is illuminated at step 420. Again, control passes back to point A on FIG. 4A.

It should be borne in mind that each consecutive data point is processed through the NOISE ANALYSIS and PATTERN ANALYSIS procedures before the next data point is processed. Consequently, only until a sufficient quantity of data points have been placed in program memory can sufficient data exist in memory to establish affirmatively either the existence of noise sufficient to light the "noise caution" lamp, or crack signatures sufficient to indicate the presence of a crack and light the "crack alarm". Such data point windows, it may be recalled, are all contained within three contiguous revolutions of the probe 50 (FIG. 1). It should be noted that a given hole may entail the storage of much more than 600 data points (three revolutions), but that less than 600 consecutive samples can result in any condition to be detected in the preferred embodiment. When all data points for the entire hole are in memory, the "inspection in progress" lamp is extinguished at 425 on FIG. 4A. If the CRACK or NOISE FLAG have been set at 430, the microcomputer at 435 activates the strip chart recorder and transfers the digitized data from memory over the data bus to the D/A converter 135 which feeds an analog signal to the strip recorder. A strip chart of the inspection is produced which reveals in analog form the eddy current signal voltage $V_s$ and the waveform which when analyzed caused the CRACK and/or NOISE FLAG to be set.

It will be appreciated that the preparation of a program which performs the steps of flow diagrams 4A through 4E on a Z80 microcomputer is within the capability of a person having ordinary skill in the art.

Description of the preferred embodiment of the present invention has been by way of example and it will be understood that various changes and modifications may be made without departing from the invention and it is intended to cover in the appended claims all such modifications and equivalents as fall within the true spirit and scope of this invention.

We claim:

1. In an apparatus for detecting discontinuities proximate the surface of a hole in a workpiece, said apparatus including a probe for radiating said workpiece with a magnetic field for inducing eddy currents in said workpiece, and said apparatus including detection means for providing input signals indicative of values of said eddy currents, said input signals assuming a characteristic signature in response to each occurrence of a detection by said detection means of one of said discontinuities, the improvement of means for receiving and analyzing said input signals comprising:
    first signature detection means operative to provide a first output signal in response to detection of a first one of said characteristic signatures;
    timing means for initiating and providing a time window of predetermined duration in response to said first output signal;
    second signature detection means operative to provide a second output signal in response to detection of a second one of said characteristic signatures; and
    crack alarm means responsive to said second output signal and said timing means for providing a crack alarm signal upon detection of said second characteristic signature within said time window.

2. In an apparatus for detecting discontinuities proximate the surface of a hole in a workpiece, said apparatus including a probe for radiating said workpiece with a magnetic field for inducing eddy currents in said workpiece, and said apparatus including detection means for providing input signals indicative of values of said eddy currents, said input signals assuming a characteristic signature in response to each occurrence of a detection by said detection means of one of said discontinuities, said signature being characterized by a first excursion of said input signals of a predetermined first polarity at or exceeding a predetermined first threshold magnitude for a predetermined first time duration, followed by a second excursion of said input signals of a predetermined second polarity opposite to said first polarity at or exceeding a predetermined second threshold magnitude for a predetermined second time duration, following by a third excursion of said input signals of said first polarity at or exceeding a predetermined third threshold magnitude for a predetermined third time duration, the improvement of means for receiving and analyzing said input signals comprising:

first peak detection means for providing a first output signal in response to detection of said first excursion of said input signal;

timing means for initiating and providing a time window of predetermined maximum duration in response to said first output signal;

second peak detection means for providing a second output signal in response to detection of said second excursion of said input signal;

third peak detection means for providing a third output signal in response to detection of said third excursion of said input signal; and     signature detection means responsive to said timing means and said second and third peak detection means for providing a signature signal in response to said second output signal followed by said third output signal within said time window.

3. The improvement of claim 2, further comprising:

signature counting means responsive to said signature signal for counting the number of said signature signals; and     discontinuity detection means responsive to said signature counting means for providing a discontinuity signal upon the the achievement of a predetermined count of said signature signals by said signature counting means.

4. The improvement of claim 2, wherein said time window is a first time window, said predetermined maximum duration is a first predetermined duration and further comprising:

second timing means for initiating and providing a second time window of a second predetermined duration in response to said signature signal; and     discontinuity detection means for providing a discontinuity signal in response to at least one subsequent occurrence of said signature signal within said second time window.

5. The improvement of claim 2, wherein said time window is a first time window, said predetermined maximum duration is a first predetermined duration and, further comprising:

second timing means for initiating and providing another time window of a second predetermined duration in response to said signature signal and at least one subsequent signature signal after the first;

signature counting means responsive to said signature signal for counting the number of signature signals comprised of the first signature signal plus subsequent signature signals occurring within their time window; and     discontinuity detection means responsive to said signature counting means for providing a discontinuity signal upon the achievement of a predetermined count of said signature signals by said signature counting means.

6. In an apparatus for detecting discontinuities proximate the surface of a hole in a workpiece, said apparatus including a probe for radiating said workpiece with a magnetic field for inducing eddy currents in said workpiece, and said apparatus including detection means for providing input signals indicative of values of said eddy currents, said input signals assuming a characteristic signature in response to each occurrence of a detection by said detection means of one of said discontinuities, said signature being characterized by a first excursion of said input signals of a predetermined first polarity at or exceeding a predetermined first threshold magnitude for a predetermined first time duration, followed by a second excursion of said input signals of a predetermined second polarity opposite to said first polarity at or exceeding a predetermined second threshold magnitude for a predetermined second time duration, followed by a third excursion of said input signals of said first polarity at or exceeding a predetermined third threshold magnitude for a predetermined third time duration, the improvement of means for receiving and analyzing said input signals comprising:

first peak detection means for providing a first output signal in response to detection of said first excursion of said input signal;

first timing means for initiating and providing a first time window of a first predetermined maximum duration in response to each occurrence of said first output signal;

second peak detection means for providing a second output signal in response to detection of said second excursion of said input signal within said first time window;

second timing means for initiating and providing a second time window of predetermined duration in response to said second output signal;

third peak detection means for providing a third output signal in response to detection of said third excursion of said input signal within said second time window; and     signature detection means for providing a signature signal in response to said third output signal.

7. The improvement of claim 6, further comprising:

third timing means for initiating and providing a third time window of a third predetermined duration in response to said signature signal; and     discontinuity detection means for providing a discontinuity signal in response to at least one subsequent occurrence of said signature signal within said third time window.

8. The improvement of claim 6, further comprising:

signature counting means responsive to said signature signal for counting the number of said signature signals; and     discontinuity detection means responsive to said signature counting means for providing a discontinuity signal upon the achievement of a predetermined count of said signature signals by said signature counting means.

9. The improvement of claim 6, further comprising:

third timing means for initiating and providing another time window of a third predetermined duration in response to said signature signal and at least one subsequent signature signal after the first;

signature counting means responsive to said signature signal for counting the number of signature signals comprised of the first signature signal plus subsequent signature signals occurring within their time window; and     discontinuity detection means responsive to said signature counting means for providing a discontinuity signal upon the achievement of a predetermined count of said signature signals by said signature counting means.

10. The improvement of claims 1, 2 or 6, further comprising:

noise peak detection means responsive to said input signal for providing a noise output signal in response to said input signal exceeding a predetermined noise threshold magnitude;

noise peak counting means responsive to said noise output signal for counting the number of said noise output signals; and noise caution means responsive to said noise peak counting means for providing a noise caution signal in response to the achievement of a predetermined count of said noise output signals by said noise peak counting means.

11. In an apparatus for detecting discontinuities proximate the surface of a hole in a workpiece, said apparatus including a probe for radiating said workpiece with a magnetic field for inducing eddy currents in said workpiece, and said apparatus including detection means for providing input signals indicative of values of said eddy current, the improvement of means for receiving and analyzing said input signals comprising:

peak detection means for providing a noise signal upon each occurrence of said input signal reaching a peak magnitude greater than a predetermined threshold magnitude;

timing means for providing a time window of a predetermined quantity of input signals;

counting means for counting occurrences of said noise signal within said time window; and warning means responsive to said counting means for providing a noise caution signal in response to said counting means counting a predetermined number of said occurrences of said noise signal within said time window.

12. A method for detecting discontinuities proximate the surface of a hole in a workpiece, comprising the steps of:

inducing an eddy current in said workpiece;

detecting said eddy current to provide an output signal;

analyzing said output signal to detect the occurrence of a first characteristic signature produced by the effect of a discontinuity upon said eddy current;

starting the timing of a timing window of predetermined duration in response to detection of the occurrence of said first characteristic signature;

analyzing said output signal to detect the occurrence of a second characteristic signature; and providing a crack alarm signal in response to the detection of the occurrence of said second characteristic signature within said timing window.

13. A method for detecting discontinuities proximate the surface of a hole in a workpiece, comprising the steps of:

inducing an eddy current in said workpiece;

detecting said eddy current to provide an output signal;

converting said output signal into a digital signal;

storing said digital signal in a memory;

analyzing said digital signal to detect the occurrence of a first peak in said digital signal;

starting the timing of a timing window of a predetermined maximum duration in response to detection of the occurrence of said first peak;

analyzing said digital signal to detect the occurrence of a second peak in said digital signal;

analyzing said digital signal to detect the occurrence of a third peak in said digital signal; and providing a crack signature signal in response to the occurrence of said second peak and said third peak within said timing window.

14. The method of claim 13 further comprising the steps of:

starting the timing of a second timing window of a second predetermined duration in response to said signature signal; and providing a crack alarm signal in response to at least one subsequent occurrence of said signature signal within said second timing window.

15. A method for detecting discontinuities proximate the surface of a hole in a workpiece, comprising the steps of:

inducing an eddy current in said workpiece;

detecting said eddy current to provide an output signal, converting said output signal into a digital signal;

storing said digital signal in a memory;

analyzing said digital signal to detect the occurrence of a first excursion of said digital signal;

starting the timing of a first timing window of a first predetermined duration in response to detection of each occurrence of said first excursion;

analyzing said digital signal to detect the occurrence of a second excursion of said digital signal within said first timing window;

starting the timing of a second timing window of a second predetermined duration in response to detection of said second excursion;

analyzing said digital signal to detect the occurrence of a third excursion of said digital signal within said second timing window;

providing a signature signal in response to each occurrence of said third excursion within said second timing window;

starting the timing of a third timing window of a third predetermined duration in response to said signature signal; and providing a crack alarm signal in response to at least one occurrence of said signature signal within said third timing window.

16. A method for detecting discontinuities proximate the surface of a hole in a workpiece, comprising the steps of:

inducing an eddy current in said workpiece;

detecting said eddy current to provide an output signal;

analyzing said output signal to detect the occurrence of a characteristic signature indicating of the presence of at least one of said discontinuities;

said signature characterized by a first excursion of said output signal of a predetermined first polarity at or exceeding a predetermined first threshold magnitude for a predetermined first time duration, followed by a second excursion of said output signal of a predetermined second polarity opposite to said first polarity at or exceeding a predetermined second threshold magnitude for a predetermined second time duration, followed by a third excursion of said output signal of said first polarity at or exceeding a predetermined third threshold magnitude for a predetermined third time duration;

analyzing said output signal to detect each occurrence of said first excursion of said signal;

starting a first timing window of a first predetermined maximum window duration in response to said first excursion;

providing a signature detection signal in response to each detection of said second excursion followed by said third excursion within said first timing window;

starting a second timing window of a predetermined second window duration in response to said signature signal; and providing a crack detection signal in response to at least one occurrence of said signature detection signal within said second timing window.

17. A method for detecting discontinuities proximate the surface of a hole in a workpiece, comprising the steps of:

inducing an eddy current in said workpiece;

detecting said eddy current to provide an output signal;

analyzing said output signal to detect the occurrence of a characteristic signature indicating of the presence of at least one of said discontinuities;

said signature characterized by a first excursion of said output signal of a predetermined first polarity at or exceeding a predetermined first threshold magnitude for a predetermined first time duration, followed by a second excursion of said output signal of a predetermined second polarity opposite to said first polarity at or exceeding a predetermined second threshold magnitude for a predetermined second time duration, followed by a third excursion of said output signal of said first polarity at or exceeding a predetermined third threshold magnitude for a predetermined third time duration;

analyzing said output signal to detect each occurrence of said first excursion of said signal;

starting a first timing window of a first predetermined window duration in response to said first excursion;

analyzing said output signal to detect each occurrence of said second excursion of said signal within said first timing window;

starting a second timing window of a second predetermined window duration in response to said second excursion;

analyzing said output signal to detect each occurrence of said third excursion of said signal within said second timing window;

providing a signature detection signal in response to detection of said third excursion within said second timing window;

starting a third timing window of a third predetermined window duration in response to said signature detection signal; and providing a crack detection signal in response to at least one occurrence of said signature detection signal within said third timing window.

* * * * *